United States Patent [19]

Tripp et al.

[11] Patent Number: 5,569,603
[45] Date of Patent: Oct. 29, 1996

[54] DIROFILARIA IMMITIS GP29 PROTEINS, NUCLEIC ACID MOLECULES AND USES THEREOF

[75] Inventors: Cynthia A. Tripp, Ft. Collins, Colo.; Murray E. Selkirk, London, England; Robert B. Grieve, Windsor, Colo.

[73] Assignee: Heska Corporation, Ft. Collins, Colo.

[21] Appl. No.: 208,885

[22] Filed: Mar. 8, 1994

[51] Int. Cl.$^6$ .................................................. C12N 15/53
[52] U.S. Cl. ........................... 435/240.1; 435/240.2; 435/240.4; 435/252.3; 435/192; 536/23.2; 536/23.7
[58] Field of Search ........................... 435/320.1, 252.3, 435/192, 240.1, 240.2, 240.4; 536/23.2, 23.7

[56] References Cited

FOREIGN PATENT DOCUMENTS

WO92/13560  8/1992  WIPO .

OTHER PUBLICATIONS

Callahan et al., pp. 245–252, 1991, Mol. Biochem. Parasitol., vol. 49.
Cookson et al., pp. 155–160, 1993, Mol. Biochem. Parasitol., vol. 58.
Cookson et al., pp. 5837–5841, 1992, Proc. Natl. Acad. Sci., vol. 89.
Devaney et al., pp. 75–87, 1991, Para. Immunol., vol. 13.
Devaney et al., pp. 365–372, 1990, Acta Tropica, vol. 47.
Flohé et al., pp. 159–169, 1971, Hoppe–Seyler's Z. Pysiol. Chem., vol. 352.
Maizels et al., pp. 249–254, 1991, Imunol. Letters, vol. 30.
Maizels et al., pp. 213–228, 1989, Mol. Biochem. Parasitol., vol. 32.
Ogilvie et al., pp. 607–618, 1990, J. Parasitol., vol. 76.
Selkirk et al., pp. 263–281, 1992, Immunobiol., vol. 184.
Selkirk et al., pp. 373–380, 1990, Acta Tropica, vol. 47.
Selkirk et al., pp. 31–43, 1990, Mol. Biochem. Parasitol., vol. 42.
Selkirk et al., pp. 91–102, 1987, Biochem. Soc. Symp., vol. 53.
Takahashi et al., pp. 677–686, 1987, Arch. Biochem. Biophys., vol. 256.
Waxman, pp. 6449–6454, 1990, Cancer Res., vol. 50.
Zvelebil et al., pp. 145–154, 1993, Mol. Biochem. Parasitol., vol. 58.
EMBL/GenBank Database #NCB1 g: : 452448, unpublished, submitted 22 Dec. 1993.

Primary Examiner—Keith D. Hendricks
Attorney, Agent, or Firm—Sheridan Ross & McIntosh

[57] ABSTRACT

The present invention relates to *D. immitis* Gp29 proteins, nucleic acid molecules having sequences that encode such proteins, antibodies raised against such proteins and inhibitors of *D. immitis* glutathione peroxidase. The present invention also includes methods to obtain such nucleic acid molecules, proteins, antibodies and inhibitors. The present invention also includes therapeutic compositions comprising such nucleic acid molecules, proteins, antibodies and inhibitors as well as their use to protect animals from disease caused by parasitic helminths, such as heartworm.

9 Claims, No Drawings

DIROFILARIA IMMITIS GP29 PROTEINS, NUCLEIC ACID MOLECULES AND USES THEREOF

FIELD OF THE INVENTION

The present invention relates to *D. immitis* Gp29 proteins, nucleic acid molecules having sequences that encode such proteins, antibodies raised against such proteins and inhibitors of *D. immitis* glutathione peroxidase. The present invention also includes therapeutic compositions comprising such nucleic acid molecules, proteins, antibodies and inhibitors, as well as their use to protect animals from disease caused by parasitic helminths, such as heartworm.

BACKGROUND OF THE INVENTION

Parasitic helminth infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasitic helminth infections, however, often leads to the development of resistant strains that no longer respond to treatment. Furthermore, many of the chemical drugs are harmful to the animals being treated, and as larger doses become required due to the build up of resistance, the side effects become even greater, It is particularly difficult to develop vaccines against parasitic helminth infections both because of the complexity of the parasite's life cycle and because, while administration of parasites or parasite antigens can lead to the production of a significant antibody response, the immune response is typically not sufficient to protect the animal against infection.

As for most parasites, the life cycle of *D. immitis*, the helminth that causes heartworm, includes a variety of life forms, each of which presents different targets, and challenges, for immunization. Adult forms of the parasite are quite large and preferentially inhabit the heart and pulmonary arteries of an animal. Males worms are typically about 12 cm (centimeters) to about 20 cm long and about 0.7 mm to about 0.9 mm wide; female worms are about 25 cm to about 31 cm long and about 1.0 to about 1.3 mm wide. Sexually mature adults, after mating, produce microfilariae which are only about 300 µm (micrometers) long and about 7 µm wide. The microfilariae traverse capillary beds and circulate in the vascular system of dogs in concentrations of about $10^3$ to about $10^5$ microfilariae per ml of blood. One method of demonstrating infection in dogs is to detect the circulating microfilariae.

If dogs are maintained in an insect-free environment, the life cycle of the parasite cannot progress. However, when microfilariae are ingested by female mosquitos during blood feeding on an infected dog, subsequent development of the microfilariae into larvae occurs in the mosquito. The microfilariae go through two larval stages (L1 and L2) and finally become mature third stage larvae (L3) of about 1.1 mm length, which can then be transmitted back to a dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilariae can be detected, but the existence of adult heartworms can be determined through thoracic examination.

Heartworm not only is a major problem in dogs, which typically cannot even develop immunity upon infection (i.e., dogs can become reinfected even after being cured by chemotherapy), but is also becoming increasingly widespread in other companion animals, such as cats and ferrets. Heartworm infections have also been reported in humans. Other parasitic helminthic infections are also widespread, and all require better treatment, including a preventative vaccine program.

One method by which parasites evade a host animal's immune system appears to be by neutralizing at least a portion of the immune response mounted by the host animal. Articles in the literature speculate that by producing an enzyme such as glutathione peroxidase, glutathione transferase and/or superoxide dismutase, parasites may resist the effects of oxidants produced by the host cellular immune system in response to infection. Cookson et al., 1992, *Proc. Natl. Acad. Sci.* 89, 5837–5841, for example, speculate that soluble forms of *Brugia glutathione* peroxidase may inhibit the oxidative burst of leukocytes (burst of hydrogen peroxide) and neutralize secondary products of lipid peroxidation, thus providing a possible explanation of why these parasites are apparently resistant to immune effector mechanisms of immune-mediated cytotoxicity.

Glutathione peroxidase has been identified in, and the gene encoding the enzyme has been cloned from, a number of organisms, including the filariid parasites *Brugia pahangi, Brugia malayi* and *Wuchereria bancrofti* as well as the trematode *Schistosoma mansoni*. The nucleotide sequence of the genes encoding *B. malayi* and *B. pahangi* glutathione peroxidases were reported to be 93.7% identical, whereas the nucleotide sequence of the genes encoding *W. bancrofti* and *B. pahangi* glutathione peroxidases were reported to be 83.1% identical; see, for example, Cookson et al., 1993, *Mol. Biochem. Parasitol.* 58, 155–160. Surface-labelling and antibody studies suggest that in Brugia, glutathione peroxidase appears to be present on L4 and adult parasites, but not on L3 parasites; see, for example, Selkirk et al., 1990, *Mol. Biochem. Parasitol.* 42, 31–43. A soluble form of glutathione peroxidase also appears to be secreted from such parasites.

Although glutathione peroxidase is a major glycoprotein of Brugia, glutathione peroxidase production in *D. immitis* is undetectable according to Callahan et al., 1991, *Mol. Biochem. Parasitol.* 49, 245–252. Callahan et al., ibid., suggest that *D. immitis* uses superoxide dismutase to protect itself from cell-mediated immunity. A review article by Selkirk et al., 1992, *Immunobiology* 184, 263–281, discloses that one drawback with glutathione peroxidase is that the protein is not observed until post-infective L3 and that, as such, a vaccine against Gp29 may not neutralize invasive larvae and may promote lymphatic pathology.

SUMMARY OF THE INVENTION

One embodiment of the present invention is an isolated nucleic acid molecule capable of hybridizing, under stringent conditions, with a *Dirofilaria immitis* Gp29 gene. Such a nucleic acid molecule can include a regulatory region of a *D. immitis* Gp29 gene and/or encode at least a portion of a D. immitis Gp29 protein. A preferred nucleic acid molecule of the present invention includes at least a portion of SEQ ID NO:1 and encodes a protein that includes at least a portion of SEQ ID NO:2. The present invention also includes recombinant molecules and recombinant cells that include nucleic acid molecules of the present invention. Also included are methods to produce nucleic acids, recombinant molecules and recombinant cells of the present invention.

Another embodiment of the present invention is an isolated protein that includes a D. immitis Gp29 protein or a mimetope of such a protein. A D. immitis Gp29 protein or mimetope of the present invention preferably has glutathione peroxidase activity and/or comprises a protein capable of eliciting an immune response against at least one epitope of D. immitis Gp29. The present invention also includes glutathione peroxidase inhibitors identified using a D. immitis Gp29 protein of the present invention as well as antibodies that recognize (i.e., selectively bind to) a D. immitis Gp29 protein and/or mimetope thereof of present invention. Also included are methods to produce D. immitis Gp29 proteins, glutathione peroxidase inhibitors and antibodies of the present invention.

Yet another embodiment of the present invention is a therapeutic composition capable of protecting an animal from disease caused by a parasitic helminth. Such a therapeutic composition includes at least one of the following protective compounds: (a) an isolated D. immitis Gp29 protein or a mimetope thereof; (b) an isolated nucleic acid molecule capable of hybridizing under stringent conditions with a D. immitis Gp29 gene; (c) an anti-D. immitis Gp29 antibody; and (d) an inhibitor of glutathione peroxidase activity identified by its ability to inhibit D. immitis glutathione peroxidase activity. Also included is a method to protect an animal from disease caused by a parasitic helminth that includes administering to the animal in an effective manner a therapeutic composition of the present invention. A preferred therapeutic composition of the present invention is a composition capable of protecting an animal from heartworm.

The present invention also includes a method to identify a compound capable of inhibiting glutathione peroxidase activity of a parasitic helminth. Such a method includes (a) contacting an isolated D. immitis Gp29 protein with a putative inhibitory compound under conditions in which, in the absence of the compound, the D. immitis Gp29 protein has glutathione peroxidase activity; and (b) determining if the putative inhibitory compound inhibits glutathione peroxidase activity. Also included is a test kit to identify a compound capable of inhibiting glutathione peroxidase activity of a parasitic helminth that includes an isolated D. immitis Gp29 protein having glutathione peroxidase activity and a means for determining the extent of inhibition of glutathione peroxidase activity in the presence of a putative inhibitory compound.

DETAILED DESCRIPTION OF THE INVENTION

The present invention includes the discovery that D. immitis does indeed express a glutathione peroxidase, referred to herein as D. immitis Gp29, despite earlier reports that glutathione peroxidase activity could not be detected in D. immitis (see, for example, Callahan et al., ibid.). D. immitis Gp29 and the gene that encodes the protein as well as homologues of the protein and of the gene are useful both in protecting animals from heartworm and in other applications, including those disclosed below.

One embodiment of the present invention is an isolated D. immitis Gp29 protein or a mimetope thereof (i.e., a mimetope of a D. immitis Gp29 protein). According to the present invention, an isolated, or biologically pure, protein, is a protein that has been removed from its natural milieu. As such, "isolated" and "biologically pure" do not necessarily reflect the extent to which the protein has been purified. An isolated D. immitis Gp29 protein can be obtained from its natural source. An isolated D. immitis Gp29 protein can also be produced using recombinant DNA technology or chemical synthesis. As used herein, an isolated D. immitis Gp29 protein can be a full-length D. immitis Gp29 protein or any homologue of such a protein, such as a D. immitis Gp29 protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol) such that the homologue has glutathione peroxidase activity and/or includes at least one epitope capable of eliciting an immune response against D. immitis Gp29 protein (i.e., when the homologue is administered to an animal as an immunogen, using techniques known to those skilled in the art, the animal will produce a humoral and/or cellular immune response against at least one epitope of D. immitis Gp29). Glutathione peroxidase activity, as well as the ability of a protein to effect an immune response, can be measured using techniques known to those skilled in the art.

A D. immitis Gp29 protein of the present invention, including a homologue of the full-length protein, has the further characteristic of being encoded by a nucleic acid molecule that is capable of hybridizing, under stringent conditions, with (i.e., to) a nucleic acid comprising at least a portion of the nucleic acid sequence encoding a D. immitis Gp29 protein, such as that disclosed in SEQ ID NO:1. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid under stringent hybridization conditions. SEQ ID NO:1 represents the deduced sequence of a cDNA (complementary DNA) nucleic acid molecule denoted $nGp29_{726}$, the production of which is disclosed in the Examples. (It should be noted that since nucleic acid sequencing technology is not entirely error-free, SEQ ID NO:1, at best, represents an apparent nucleic acid sequence of the nucleic acid molecule encoding at least a portion of D. immitis Gp29.) As used herein, stringent hybridization conditions refer to standard hybridization conditions under which nucleic acid molecules (or sequences), including oligonucleotides, are used to identify similar sequences. Such standard conditions are disclosed, for example, in Sambrook et al., *Molecular Cloning: A Laboratory Manual*, Cold Spring Harbor Labs Press, 1989. Examples of such conditions are provided in the Examples section. Preferred D. immitis Gp29 proteins of the present invention are encoded by nucleic acid sequences having at least about 80 percent homology (identity within comparable regions) with the nucleic acid sequence of SEQ ID NO:1. More preferred D. immitis Gp29 proteins of the present invention are encoded by nucleic acid sequences having at least about 85 percent homology with SEQ ID NO:1, and even more preferred D. immitis Gp29 proteins of the present invention are encoded by nucleic acid sequences having at least about 90 percent homology with SEQ ID NO:1.

D. immitis Gp29 protein homologues can be the result of natural allelic variation or natural mutation. D. immitis Gp29 protein homologues can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to effect glutathione peroxidase activity and/or to elicit an immune response against *D. immitis* Gp29 proteins. Examples of such identification techniques are disclosed herein.

The minimum size of an isolated protein of the present invention is sufficient to form an epitope, a size that is typically at least from about 7 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

In accordance with the present invention, a mimetope refers to any compound that is able to mimic the ability of an isolated *D. immitis* Gp29 protein of the present invention. A mimetope can be a peptide that has been modified to decrease its susceptibility to degradation but that still retains glutathione peroxidase activity and/or the ability to elicit an immune response against at least one epitope of *D. immitis* Gp29. Other examples of mimetopes include, but are not limited to, anti-idiotypic and/or catalytic antibodies, or fragments thereof capable of mimicking the enzyme activity or that include at least one binding site that mimics one or more epitopes of a *D. immitis* Gp29 protein; non-proteinaceous immunogenic portions of an isolated protein (e.g., carbohydrate structures); and synthetic or natural organic molecules, including nucleic acids, that have a structure similar to at least one epitope of an isolated protein of the present invention. Such mimetopes can be obtained, for example, by affinity chromatography techniques using antibodies raised against a *D. immitis* Gp29 protein of the present invention or by a screen for a molecule having glutathione peroxidase activity.

A preferred *D. immitis* Gp29 protein or mimetope of the present invention is a compound that when administered to an animal in an effective manner, is capable of protecting that animal from disease caused by a parasitic helminth. The parasitic helminth preferably is essentially incapable of causing disease in an animal that is immunized with a *D. immitis* Gp29 protein of the present invention. In accordance with the present invention, the ability of a protein or mimetope of the present invention to protect an animal from disease by a parasitic helminth refers to the ability of that protein or mimetope to treat, ameliorate and/or prevent disease, including infection leading to disease, caused by the parasitic helminth, preferably by eliciting an immune response against the helminth. Such an immune response can include humoral and/or cellular immune responses.

A suitable parasitic helminth of the present invention is a parasitic helminth that is essentially incapable of causing disease in an animal administered a *D. immitis* Gp29 protein of the present invention. As such, a parasitic helminth of the present invention includes any parasitic helminth that produces a protein having one or more epitopes that can be targeted by a humoral and/or cellular response against a *D. immitis* Gp29 protein of the present invention and/or that can be targeted by a compound that is capable of substantially inhibiting *D. immitis* glutathione peroxidase activity, thereby resulting in the reduced ability of the parasitic helminth to cause disease in an animal. Suitable helminth parasites to target include nematodes, cestodes and trematodes, with filariid, ascarid, strongyle and trichostrongyle nematodes being preferred. More preferred parasitic helminths to target include parasites of the genera Aelurostrongylus, Ancylostoma, Angiostrongylus, Ascaris, Brugia, Bunostomum, Capillaria, Chabertia, Cooperia, Dictyocaulus, Dipetalonema, Dirofilaria, Dracunculus, Enterobius, Haemonchus, Loa, Mansonella, Necator, Nematodirus, Oesophagostomum, Onchocerca, Ostertagia, Parafilaria, Parascaris, Protostrongylus, Setaria, Strongyloides, Strongylus, Toxascaris, Toxocara, Toxoplasma, Trichinella, Trichostrongylus, Trichuris, Uncinaria and Wuchereria. Also preferred are nematodes of the order Ascaridida (Ascarids) and Cyathostominae (small strongyles of horses). A particularly preferred parasitic helminth to target is *D. immitis*, the parasite that causes heartworm.

One embodiment of the present invention is a fusion protein that includes a *D. immitis* Gp29-containing domain attached to a fusion segment. Inclusion of a fusion segment as part of a *D. immitis* Gp29 protein of the present invention can enhance the protein's stability during production, storage and/or use. Depending on the segment's characteristics, a fusion segment can also act as an immunopotentiator to enhance the immune response mounted by an animal immunized with a *D. immitis* Gp29 protein containing such a fusion segment. Furthermore, a fusion segment can function as a tool to simplify purification of a *D. immitis* Gp29 protein, such as to enable purification of the resultant fusion protein using affinity chromatography. A suitable fusion segment can be a domain of any size that has the desired function (e.g., increased stability, increased immunogenicity, and/or purification tool). It is within the scope of the present invention to use one or more fusion segments. Fusion segments can be joined to amino and/or carboxyl termini of the *D. immitis* Gp29-containing domain of the protein. Linkages between fusion segments and *D. immitis* Gp29-containing domains of fusion proteins can be susceptible to cleavage in order to enable straight-forward recovery of the *D. immitis* Gp29-containing domains of such proteins. Fusion proteins are preferably produced by culturing a recombinant cell transformed with a fusion nucleic acid molecule that encodes a protein including the fusion segment attached to either the carboxyl and/or amino terminal end of a *D. immitis* Gp29-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include βGAL-PGp29$_{726}$, PHIS-PGp29$_{658}$, PTRP-PGp29$_{658}$ and PMALB-PGp29$_{658}$, the production of which is disclosed herein.

Another embodiment of the present invention is a *D. immitis* Gp29 protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent. Examples of multivalent protective compounds include, but are not limited to, a *D. immitis* Gp29 protein attached to one or more other *D. immitis* proteins or a *D. immitis* Gp29 protein attached to one or more compounds protective against one or more other infectious agents, particularly an agent that infects cats or dogs, such as, but not limited to, calicivirus, distemper virus, feline herpesvirus, feline immunodeficiency virus, feline leukemia virus, feline infectious peritonitis, hepatitis, hookworm, leptospirosis, panleukopenia virus, parvovirus, rabies and toxoplasmosis.

Suitable other *D. immitis* proteins to include with a *D. immitis* Gp29 protein in a multivalent protective protein include, but are not limited to, a *D. immitis* P39 protein, a *D. immitis* P22U protein, a *D. immitis* P22L protein, a *D. immitis* P20.5 protein, a *D. immitis* P4 protein, a *D. immitis* Di22 protein and/or a *D. immitis* protease expressed in L3 and/or L4 larvae, as well as other helminth proteins sharing significant homology with such *D. immitis* proteins. A protein sharing significant homology with another protein refers to the ability of the nucleic acid sequences encoding such proteins to form stable hybridization complexes with each other under stringent hybridization conditions, as described, for example, in Sambrook et al., ibid. U.S. patent application Ser. No. 08/003,389, filed Jan. 12, 1993, entitled "Immunogenic Larval Proteins", discloses a 39-kD (kilodalton) *D. immitis* protein (size determined by Tris glycine SDS-PAGE (sodium dodecyl sulfate polyacrylamide gel electrophoresis)), referred to herein as P39, and a nucleic acid sequence that encodes it. U.S. patent application Ser. No. 08/003,257, filed Jan. 12, 1993, entitled "Reagents and Methods for Identification of Vaccines" discloses 22-kD and 20.5-kD *D. immitis* proteins (sizes determined by Tris glycine SDS-PAGE), referred to herein as P22L and P20.5, and nucleic acid sequences that encode them. U.S. patent application Ser. No. 08/109,391, filed Aug. 19, 1993, entitled "Novel Parasitic Helminth Proteins" discloses *D. immitis* P4 and *D. immitis* P22U, as well as nucleic acid sequences that encode them. U.S. patent application Ser. No. 08/060,500, filed May 10, 1993, entitled "Heartworm Vaccine", discloses a *D. immitis* Di22 protein and a nucleic acid sequence encoding it (included in Genbank data base accession number M82811); Ser. No. 08/060,500 is a continuation of U.S. patent application Ser. No. 07/683,202, filed Ap. 8, 1991. U.S. patent application Ser. No. 08/153,554, filed Nov. 16, 1993, entitled "Protease Vaccine Against Heartworm", discloses *D. immitis* larval proteases; Ser. No. 08/153,554 is a continuation of U.S. patent application Ser. No. 07/792,209, filed Nov. 12, 1991. Each of these patent applications is incorporated by reference herein in its entirety.

A particularly preferred *D. immitis* Gp29 protein is a protein encoded by at least a portion of SEQ ID NO:1 and, as such is a protein having an amino acid sequence that includes at least a portion of SEQ ID NO:2. The deduced translation of SEQ ID NO:1 (representative of the nucleic acid sequence of nucleic acid molecule $nGp29_{726}$), represented in SEQ ID NO:2 (representative of *D. immitis* Gp29 protein $PGp29_{219}$), suggests that a full-length *D. immitis* Gp29 protein includes an open reading frame of at least about 219 amino acids followed by a stop codon. The translation start site of $nGp29_{726}$ is as yet unknown, but SEQ ID NO:1 is likely to represent almost all of the coding region, since the deduced amino acid sequence SEQ ID NO:2 suggests a protein having a molecular weight of about 29 kD and an estimated pI of about 5.89. The amino acid sequence of SEQ ID NO:2 is about 37 percent homologous to human plasma glutathione peroxidase, about 42 percent homologous to human liver glutathione peroxidase, about 73 percent homologous to *W. bancrofti* Gp29 and about 74 percent homologous to both *B. malayi* Gp29 and to *B. pahangi* Gp29.

An interesting characteristic of *D. immitis* $PGp29_{219}$ is that, unlike mammalian glutathione peroxidases, *D. immitis* $PGp29_{219}$ apparently is not a selenoprotein. Known coding regions of mammalian glutathione peroxidases, which require selenium in order to effect glutathione-mediated reduction of toxic peroxides, include an opal codon that is translated as a selenocysteine. In contrast, SEQ ID NO:1 has the cysteine codon UCU in the corresponding position; *W. bancrofti*, *B. malayi* and *B. pahangi* Gp29 nucleic acid sequences have UGC cysteine codons at the corresponding position. While not being bound by theory, it is believed that filariid glutathione peroxidase activity does not require selenium.

Another embodiment of the present invention is a *D. immitis* Gp29 protein that includes an amino acid sequence having at least about 75 percent, preferably at least about 80 percent, more preferably at least about 85 percent and even more preferably at least about 90 percent homology with the corresponding region(s) of the amino acid sequence of SEQ ID NO:2.

Particularly preferred proteins of the present invention include $PGp29_{219}$, proteins that include $PGp29_{219}$ (such as, but not limited to, full-length *D. immitis* Gp29 proteins, fusion proteins and proteins providing multivalent protection) and proteins that are truncated homologues of $PGp29_{219}$. Even more preferred proteins include $PGp29_{219}$, $\beta GAL\text{-}PGp29_{726}$, $PHIS\text{-}PGp29_{658}$, $PTRP\text{-}PGp29_{658}$ and $PMALB\text{-}PGp29_{658}$. Examples of methods to produce $PGp29_{219}$, $\beta GAL\text{-}PGp29_{726}$ and $PHIS\text{-}PGp29_{658}$, $PTRP\text{-}PGP29_{658}$ are disclosed in the Examples section. $pMALB\text{-}PGp29_{658}$, a fusion protein that includes a maltose binding domain, can be produced in a recombinant cell transformed with a recombinant molecule comprising $nGp29_{658}$ operatively linked to a pMAL vector (e.g., pMAL-c2 or pMAL-c5, available from New England BioLabs, Beverly, Mass.). Such recombinant molecules include $pMal2\text{-}nGp29_{658}$ and $pMal5\text{-}nGp29_{658}$.

Another embodiment of the present invention is an isolated nucleic acid molecule capable of hybridizing, under stringent conditions, with a *D. immitis* Gp29 gene. As used herein, a *D. immitis* Gp29 gene includes all nucleic acid sequences related to a natural *D. immitis* Gp29 gene such as regulatory regions that control production of a *D. immitis* Gp29 protein encoded by that gene (such as, but not limited to, transcription, translation or post-translation control regions) as well as the coding region itself. A *D. immitis* Gp29 nucleic acid molecule of the present invention can include an isolated natural *D. immitis* Gp29 gene or a homologue thereof. A nucleic acid molecule of the present invention can include one or more regulatory regions, full-length or partial coding regions, or combinations thereof. The minimal size of a *D. immitis* nucleic acid molecule of the present invention is the minimal size capable of forming a stable hybrid under stringent hybridization conditions.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated *D. immitis* Gp29 nucleic acid molecule of the present invention can be obtained from its natural source either as an entire (i.e., complete) gene or a portion thereof capable of forming a stable hybrid with that gene. An isolated *D. immitis* Gp29 nucleic acid molecule can also be produced using recombinant DNA technology (e.g., polymerase chain reaction (PCR) amplification, cloning) or chemical synthesis. Isolated *D. immitis* Gp29 nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a *D. immitis* Gp29 protein of the present invention or to form stable hybrids under stringent conditions with natural isolates.

A *D. immitis* Gp29 nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., glutathione peroxidase activity or ability to elicit an immune response against at least one epitope of a *D. immitis* Gp29 protein) and/or by hybridization with isolated *D. immitis* Gp29 nucleic acids under stringent conditions.

An isolated nucleic acid molecule of the present invention can include a nucleic acid sequence that encodes at least one of *D. immitis* Gp29 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a *D. immitis* Gp29 protein. As heretofore disclosed, *D. immitis* Gp29 proteins of the present invention include, but are not limited to, proteins having full-length *D. immitis* Gp29 coding regions, proteins having partial *D. immitis* Gp29 coding regions, fusion proteins, multivalent protective proteins and combinations thereof.

One embodiment of the present invention is a *D. immitis* Gp29 nucleic acid molecule that includes a nucleic acid sequence having at least about 80 percent, preferably at least about 85 percent, more preferably at least about 90 percent and even more preferably at least about 95 percent homology with the corresponding region(s) of the nucleic acid sequence of SEQ ID NO:1.

A preferred nucleic acid molecule of the present invention includes at least a portion of nGp29$_{726}$. As such, a preferred nucleic acid molecule of the present invention includes a nucleic acid sequence including at least a portion of SEQ ID NO:1. Such a nucleic acid molecule can be nGp29$_{726}$, can include nucleotides in addition to nGp29$_{726}$ (such as, but not limited to, a full-length gene, a nucleic acid molecule encoding a fusion protein, or a nucleic acid molecule encoding a multivalent protective compound), or can be a truncation fragment of nGp29$_{726}$. Particularly preferred nucleic acid molecules include nGp29$_{726}$, nGP29$_{658}$ and nGp29$_{660}$.

The present invention also includes nucleic acid molecules encoding at least a portion of SEQ ID NO:2, including nucleic acid molecules that have been modified to accommodate codon usage properties of the cells in which such nucleic acid molecules are to be expressed.

Knowing the nucleic acid sequence of nGp29$_{726}$ allows one skilled in the art to make copies of that nucleic acid molecule as well as to obtain nucleic acid molecules including at least a portion of nGp29$_{726}$ (e.g., molecules that also include the translation start site and/or transcription and/or translation control regions), nucleic acid molecules including portions of nGp29$_{726}$ and other *D. immitis* Gp29 nucleic acid molecule homologues. Such nucleic acid molecules can be obtained in a variety of ways including screening appropriate expression libraries with antibodies of the present invention or glutathione peroxidase screening assays; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify include *D. immitis* L3 cDNA, *D. immitis* L4 cDNA, adult *D. immitis* cDNA or *D. immitis* genomic DNA libraries. Similarly, preferred DNA sources to screen or from which to amplify include *D. immitis* L3 cDNA, *D. immitis* L4 cDNA, adult *D. immitis* cDNA or *D. immitis* genomic DNA. Techniques to clone and amplify genes are disclosed, for example, in Sambrook et al., ibid.

The present invention also includes nucleic acid molecules that are oligonucleotides capable of hybridizing, under stringent conditions, with complementary regions of other, preferably longer, nucleic acid molecules of the present invention, such as to complementary regions of *D. immitis* nucleic acid molecule nGp29$_{726}$, complementary regions of nucleic acid molecules that include at least a portion of nGp29$_{726}$, and complementary region of nucleic acid molecules that hybridize under stringent conditions with nGp29$_{726}$. Such oligonucleotides can be RNA, DNA, or derivatives of either. The minimal size of such oligonucleotides is the size required to form a stable hybrid between a given oligonucleotide and the complementary sequence on another nucleic acid molecule of the present invention. As such, the size is dependent on nucleic acid composition and percent homology between the oligonucleotide and complementary sequence as well as upon hybridization conditions per se (e.g., temperature, salt concentration). For AT-rich nucleic acid sequences, such as those of *D. immitis*, oligonucleotides typically are at least about 15 to about 17 bases in length. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of *D. immitis* glutathione peroxidase by a heartworm. Such therapeutic applications include the use of such oligonucleotides in, for example, antisense-, triplex formation-, ribozyme- and/or RNA drug-based technologies. The present invention, therefore, includes such oligonucleotides and methods to interfere with the production of D. immitis Gp29 proteins by use of one or more of such technologies. Appropriate oligonucleotide-containing therapeutic compositions can be administered to an animal, using techniques known to those skilled in the art, either prior to or after infection by a parasitic helminth such as D. immitis in order to protect the animal from disease.

The present invention also includes a recombinant vector, which includes a D. immitis Gp29 nucleic acid molecule of the present invention inserted into any vector capable of delivering the nucleic acid molecule into a host cell. Such a vector contains heterologous nucleic acid sequences, that is nucleic acid sequences that are not naturally found adjacent to D. immitis Gp29 nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of D. immitis Gp29 nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

A preferred nucleic acid molecule to include in a recombinant vector of the present invention is a nucleic acid molecule that includes at least a portion of $nGp29_{726}$. Particularly preferred nucleic acid molecules to include in recombinant vectors of the present invention include $nGp29_{726}$, $nGp29_{658}$ and $nGp29_{660}$.

Isolated proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. A preferred nucleic acid molecule with which to transform a cell is a nucleic acid molecule that includes at least a portion of $nGp29_{726}$. Particularly preferred nucleic acid molecules with which to transform cells include $nGp29_{726}$, $nGP29_{658}$ and $nGP29_{660}$.

Suitable host cells to transform include any cell that can be transformed. Host cells can be either untransformed cells or cells that are already transformed with at least one nucleic acid molecule. Host cells of the present invention either can be endogenously (i.e., naturally) capable of producing D. immitis Gp29 proteins of the present invention or can be capable of producing such proteins after being transformed with at least one nucleic acid molecule of the present invention. Host cells of the present invention can be any cell capable of producing a D. immitis Gp29 protein of the present invention, including bacterial, fungal (including yeast), animal parasite (including helminth), insect, animal and plant cells. Preferred host cells include bacterial, mycobacterial, yeast, helminth, insect and mammalian cells. More preferred host cells include Salmonella, Escherichia, Bacillus, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation) and COS cells. Particularly preferred host cells are Escherichia coli, including E. coli K-12 derivatives; Salmonella typhi; Salmonella typhimurium, including attenuated strains such as UK-1 $_x$3987 and SR-11 $_x$4072; Spodoptera frugiperda; Trichoplusia ni; BHK cells; MDCK cells; CRFK cells and non-tumorigenic mouse myoblast G8 cells (e.g., ATCC CRL 1246). Additional appropriate mammalian cell hosts include other kidney cell lines (e.g., CV-1 monkey kidney cell lines), other fibroblast cell lines (e.g., human, murine or chicken embryo fibroblast cell lines), myeloma cell lines, Chinese hamster ovary cells and/or HeLa cells.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e.,direct gene expression) in recombinant cells of the present invention, including in bacterial, fungal, animal parasite, insect, animal, and plant cells. Preferred expression vectors of the present invention can direct gene expression in bacterial, yeast, helminth, insect and mammalian cells and more preferably in the cell types heretofore disclosed.

Expression vectors of the present invention may also contain secretory signals (i.e., signal segment nucleic acid sequences) to enable an expressed D. immitis Gp29 protein to be secreted from the cell that produces the protein and/or contain fusion sequences which lead to the expression of inserted nucleic acid molecules of the present invention as fusion proteins. Eukaryotic recombinant molecules may include intervening and/or untranslated sequences surrounding and/or within the nucleic acid sequences of D. immitis Gp29 nucleic acid molecules. Examples of suitable fusion segments encoded by fusion segment nucleic acids have been disclosed. Suitable signal segments include a D. immitis Gp29 signal segment or any heterologous signal segment capable of directing the secretion of a D. immitis Gp29 protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a *D. immitis* Gp29 molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. Examples of preferred recombinant molecules are heretofore described. Particularly preferred recombinant molecules include pβgal-nGP $29_{726}$, pHis-nGP$29_{658}$, pTrp-nGp$29_{658}$, pTECH-nGp$29_{726}$, pTECH-nGp$29_{658}$, pMal2-nGp$29_{658}$, pMal5-nGp$29_{658}$, p$\lambda P_R$-nGP$29_{658}$, p$\lambda P_L$-nGp$29_{658}$, pBBIII-nGp$29_{658}$ and pToto2J1-nGp$29_{658}$. Details regarding the production of such recombinant molecules is disclosed herein.

A recombinant cell of the present invention includes any cells transformed with at least one of any nucleic acid molecule of the present invention. A preferred recombinant cell is a cell transformed with a nucleic acid molecule that includes at least a portion of nGp$29_{726}$. Particularly preferred recombinant cells include *E. coli*:pβgal-nGp$29_{726}$, *E.coli*:pHis-nGp$29_{658}$, *E.coli*:pTrp-nGp$29_{658}$, Salmonella:pTECH-nGp$29_{726}$, Salmonella:pTECH-nGp$29_{658}$, *E.coli*:pMal2-nGp$29_{658}$, *E.coli*:pMal5-nGp$29_{658}$, *E.coli*:p$\lambda P_R$-nGp $29_{658}$, *E. coli*:p$\lambda P_L$-nGp$29_{658}$, *S. frugiperda*:pBBIII-nGp$29_{658}$ and BHK:pToto2J1-nGp$29_{658}$.

Recombinant cells of the present invention can also be co-transformed with one or more recombinant molecules including nucleic acid molecules encoding one or more *D. immitis* Gp29 nucleic acid molecules and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce a *D. immitis* Gp29 protein of the present by culturing such cells under conditions effective to produce such a protein, and recovering the protein. Effective conditions to produce a protein include, but are not limited to, appropriate media, bioreactor, temperature, pH and oxygen conditions that permit protein production. An appropriate medium refers to any medium in which a cell of the present invention, when cultured, is capable of producing a *D. immitis* Gp29 protein. An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant *D. immitis* Gp29 proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. *D. immitis* Gp29 proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. *D. immitis* Gp29 proteins are preferably retrieved in "substantially pure" form. As used herein, "substantially pure" refers to a purity that allows for the effective use of the protein as a therapeutic composition or diagnostic. A vaccine for animals, for example, should exhibit no substantial toxicity and should be capable of stimulating the production of antibodies in a vaccinated animal.

The present invention also includes antibodies capable of selectively binding to a *D. immitis* Gp29 protein or mimetope thereof. Such an antibody is herein referred to as an anti-*D. immitis* Gp29 antibody. As used herein, the term "selectively binds to" refers to the ability of such an antibody to preferentially bind to *D. immitis* Gp29 proteins and mimetopes thereof. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to proteins, or mimetopes thereof, that are encoded, at least in part, by a *D. immitis* Gp29 nucleic acid molecule.

A preferred method to produce antibodies of the present invention includes administering to an animal an effective amount of a *D. immitis* Gp29 protein or mimetope thereof to produce the antibody and recovering the antibodies. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from parasitic helminths susceptible to treatment by such antibodies, (b) as reagents in assays to detect infection by such parasitic helminths and/or (c) as tools to recover desired *D. immitis* Gp29 proteins from a mixture of proteins and other contaminants.

Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents include, but are not limited to: double-chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but lack the toxin's intrinsic cell binding domain.

One embodiment of the present invention is a therapeutic composition that, when administered to an animal in an effective manner, is capable of protecting that animal from disease caused by a parasitic helminth. Such a parasitic helminth is susceptible to at least one of the following treatments: administration of inhibitors of *D. immitis* glutathione peroxidase activity or immunization with an isolated *D. immitis* Gp29 protein. As used herein, a parasitic helminth that is susceptible to such a treatment is a parasitic helminth that, if such treatment is administered to an animal in an effective manner, shows substantially reduced ability to cause disease in the animal. It is to be understood that such parasitic helminths can be susceptible to treatments other than just glutathione peroxidase inhibition or immunization with a *D. immitis* Gp29 protein, including, but not limited to additional treatments, or therapeutic compositions, disclosed herein.

Therapeutic compositions of the present invention include at least one of the following protective compounds: (a) an isolated *D. immitis* Gp29 protein or a mimetope thereof, (b) an isolated nucleic acid molecule capable of hybridizing under stringent conditions a *D. immitis* Gp29 gene, (c) an anti-*D. immitis* Gp29 antibody and (d) an inhibitor of glutathione peroxidase activity identified by its ability to inhibit *D. immitis* glutathione peroxidase activity. As used herein, a protective compound refers to a compound that, when administered to an animal in an effective manner, is able to treat, ameliorate, and/or prevent disease caused by a parasitic helminth of the present invention. Preferred parasitic helminths to target are heretofore disclosed. Examples of *D. immitis* Gp29 proteins, *D. immitis* Gp29 nucleic acid molecules and *D. immitis* Gp29 antibodies, including immunotoxins, are disclosed above. Glutathione peroxidase inhibitors of the present invention are described in more detail below.

The present invention also includes a therapeutic composition comprising at least one *D. immitis* Gp29-based protective compound of the present invention in combination with at least one additional compound protective against one or more infectious agents. In one embodiment, a therapeutic composition of the present invention includes (a) at least one of the following: an isolated *D. immitis* Gp29 protein or a mimetope thereof, an isolated *D. immitis* Gp29 nucleic acid molecule, an anti-*D. immitis* Gp29 antibody or an inhibitor of *D. immitis* glutathione peroxidase activity in addition to (b) at least one of the following compounds: (i) a *D. immitis* P39 protein, a *D. immitis* P22U protein, a *D. immitis* P22L protein, a *D. immitis* P20.5 protein, a *D. immitis* P4 protein, a *D. immitis* Di22 protein, a *D. immitis* protease expressed in L3 and/or L4 larvae or another helminth protein sharing significant homology with such *D. immitis* proteins; (ii) mimetopes of any of such proteins; (iii) nucleic acid molecules encoding any of such proteins; and (iv) antibodies that selectively bind to any of such proteins. Therapeutic compositions of the present invention can also include protective compounds against other diseases such as calicivirus, distemper virus, feline herpesvirus, feline immunodeficiency virus, feline leukemia virus, feline infectious peritonitis, hepatitis, hookworm, leptospirosis, panleukopenia virus, parvovirus, rabies and toxoplasmosis.

Therapeutic compositions of the present invention can be administered to any animal, preferably to mammals, and more preferably to dogs, cats, humans, ferrets, horses, cattle, sheep and other pets and/or economic food animals. Preferred animals to protect include dogs, cats, humans and ferrets, with dogs and cats being particularly preferred.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

In order to protect an animal from disease caused by a parasitic helminth of the present invention, a therapeutic composition of the present invention is administered to the animal in an effective manner such that the composition is capable of protecting that animal from disease. For example, an isolated protein or mimetope thereof, when administered to an animal in an effective manner, is able to elicit (i.e., stimulate) an immune response, preferably including both a humoral and cellular response, that is sufficient to protect the animal from disease. Similarly, an antibody of the present invention, when administered to an animal in an effective manner, is administered in an amount so as to be present in the animal at a titer that is sufficient to protect the animal from disease, at least temporarily. Oligonucleotide nucleic acid molecules of the present invention can also be administered in an effective manner, thereby reducing expression of Gp29 proteins in order to interfere with development of parasitic helminths of the present invention.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram (µg) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 µg to about 1 mg of the vaccine per kg body weight of the animal is administered from about one to about two times over a time period of from about 2 weeks to about 12 months. Modes of administration can include, but are not limited to, subcutaneous, intradermal, intravenous, nasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) direct injection (e.g., as "naked" DNA or RNA molecules, such as is taught, for example in Wolff et al., 1990, *Science* 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015,414, filed Feb. 8, 1993, entitled "Recombinant Virus Particle Vaccines", which is incorporated by reference herein in its entirety.

When administered to an animal, a recombinant virus particle vaccine of the present invention infects cells within the immunized animal and directs the production of a *D. immitis* Gp29 protein or RNA nucleic acid molecule that is capable of protecting the animal from disease caused by a parasitic helminth of the present invention. For example, a recombinant virus particle comprising a *D. immitis* Gp29 nucleic acid molecule, such as $nGp29_{726}$ is administered according to a protocol that results in the animal producing a sufficient immune response to protect itself from heartworm. A preferred single dose of a recombinant virus particle vaccine of the present invention is from about $1\times10^4$ to about $1\times10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one *D. immitis* Gp29 protein. Preferred recombinant cells include Salmonella, *E. coli*, Mycobacterium, *S. frugiperda*, baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

In common with most other enteric pathogens, Salmonella strains normally enter the host orally. Once in the intestine, they interact with the mucosal surface, normally to establish an invasive infection. Most Salmonella infections are controlled at the epithelial surface, causing the typical Salmonella-induced gastroenteritis. Some strains of Salmonella, including *S. typhi* and some *S. typhimurium* isolates, have evolved the ability to penetrate deeper into the host, causing a disseminated systemic infection. It appears such strains have the capacity to resist the killing actions of macrophages and other immune cells. *S. typhi* can exist for long periods as a facultative intracellular parasite. Some of the live vaccine strains can also persist for long periods in the mononuclear phagocyte system. Hosts infected in such a manner develop, in addition to a mucosal immune response, systemic cellular and serum antibody responses to the Salmonella. Thus, invading Salmonella, whether virulent or attenuated, can stimulate strong immune responses, unlike many other enteric pathogens which only set up local, noninvasive gut infections. The potent immunogenicity of live Salmonella makes them attractive candidates for carrying *D. immitis* Gp29 proteins to the immune system.

A preferred recombinant cell-based vaccine is one in which the cell is attenuated. *Salmonella typhimurium* strains, for example, can be attenuated by introducing mutations into genes critical for in vivo growth and survival. For example, genes encoding cyclic adenosine monophosphate (cAMP) receptor protein or adenylate cyclase are deleted to produce avirulent, vaccine strains. Such strains can deliver antigens to lymphoid tissue in the gut but demonstrate reduced capacity to invade the spleen and mesenteric lymph nodes. These strains are still capable of stimulating both humoral and cellular immunity in mammalian hosts.

Recombinant cell vaccines can be used to introduce *D. immitis* Gp29 proteins of the present invention into the immune systems of animals. For example, recombinant molecules comprising *D. immitis* Gp29 nucleic acid molecules of the present invention operatively linked to expression vectors that function in Salmonella can be transformed into Salmonella host cells. The resultant recombinant cells are then introduced into the animal to be protected. Preferred Salmonella host cells are those for which survival depends on their ability to maintain the recombinant molecule (i.e., a balanced-lethal host-vector system). An example of such a preferred host/recombinant molecule combination is a Salmonella strain (e.g., UK-1 $_\chi$3987 or SR-11 $_\chi$4072) which is unable to produce aspartate β-semialdehyde dehydrogenase in combination with a recombinant molecule also capable of encoding the enzyme. Aspartate β-semialdehyde dehydrogenase, encoded by the asd gene, is an important enzyme in the pathway to produce diaminopimelic acid (DAP). DAP is an essential component of the peptidoglycan of the cell wall of Gram-negative bacteria, such as Salmonella, and, as such, is necessary for survival of the cell. Thus, Salmonella lacking a functional asd gene can only survive if they maintain a recombinant molecule that is also capable of expressing a functional asd gene.

In one embodiment, a nucleic acid molecule of the present invention, such as nGp29$_{726}$ or nGp29$_{658}$, is inserted into expression vector pTECH-1 (available from Medeva, London, U.K.) and the resulting recombinant molecule, e.g., pTECH-nGp29$_{726}$ or pTECH-nGp29$_{658}$, is transfected into a Salmonella strain, such as BRD 509 (available from Medeva), to form a recombinant cell, e.g., Salmonella:pTECH-nGp29$_{726}$ or Salmonella:pTECH-nGp29$_{658}$. Such recombinant cells can be used to produce the corresponding encoded Gp29 protein or can be used as recombinant cell vaccines.

One preferred embodiment of the present invention is the use of *D. immitis* Gp29 nucleic acid molecules and proteins to protect an animal from heartworm. Although it is particularly preferred to prevent L3 larvae that are delivered to the animal by the mosquito and L4 larvae from maturing into adult worms, the present invention also includes means to inhibit adult worms, since Gp29 is expressed in all three stages. Preferred therapeutic compositions are those that are able to inhibit at least one step in the portion of the parasite's development cycle that includes L3 larvae, third molt, L4 larvae, fourth molt and immature adult prior to entering the circulatory system. In dogs, this portion of the development cycle is about 70 days. As such, preferred therapeutic compositions include *D. immitis* Gp29 nucleic acid molecules, *D. immitis* Gp29 proteins and mimetopes thereof, anti-*D. immitis* Gp29 antibodies and inhibitors of *D. immitis* glutathione peroxidase activity. Such compositions are administered to animals in a manner effective to protect the animals from heartworm. Additional protection may be obtained by administering additional protective compounds, including other *D. immitis* proteins, nucleic acid molecules and antibodies as heretofore disclosed.

One therapeutic composition of the present invention includes an inhibitor of *D. immitis* glutathione peroxidase activity, i.e., a compound capable of substantially interfering with the function of a parasitic helminth glutathione peroxidase susceptible to inhibition by an inhibitor of *D. immitis* glutathione peroxidase activity.

As heretofore disclosed, parasite glutathione peroxidases appear to help the parasite evade the host immune system, thereby allowing the parasite to survive and multiply for years. Heartworm, for example, can exist for many years in the circulatory system of an animal. Without being bound by theory, parasite glutathione peroxidases are believed to function as antioxidants that scavenge or quench reactive oxygen species that are produced by host cell-mediated immune responses, thereby protecting parasite cellular membranes and other cellular components. Proposed functions of parasite glutathione peroxidases include neutralization (i.e., reduction) of fatty acid- and lipid-hyperperoxides, including harmful products of lipid peroxidation. It has recently been proposed that another function of parasite glutathione peroxidases is to catalyze the formation of tyrosine cross-linking residues, such as dityrosine, trityrosine and isotrityrosine, which are important components of the parasite's cuticle. Stages of expansive growth by parasites appear to be accompanied by increased levels of cross-linking of collagens and epicuticle proteins to maintain the integrity of the cuticle. Temporal expression of *D. immitis* Gp29 also appears to correlate with such developmental phases. While not being bound by theory, it is also believed that a highly cross-linked surface may serve to protect parasites from immune attack.

As such, an inhibitor of parasite glutathione peroxidase activity is valuable in blocking parasite growth and development. Such an inhibitory compound can be identified using *D. immitis* Gp29 proteins of the present invention. One embodiment of the present invention is a method to identify a compound capable of inhibiting parasite glutathione peroxidase activity that includes (a) contacting an isolated *D. immitis* Gp29 protein with a putative inhibitory compound under conditions in which, in the absence of said compound, the *D. immitis* Gp29 protein has glutathione peroxidase activity; and (b) determining if the putative inhibitory compound inhibits glutathione peroxidase activity. Putative inhibitory compounds to screen include organic molecules, antibodies (including functional equivalents thereof) and glutathione analogs; see, for example, Waxman, 1990, *Cancer Res.* 50, 6449–6454 and Flohe et al., 1971, *Hoppe-Seyler's Z. Physiol. Chem.* 352, 159–169. Methods to determine glutathione peroxidase activity are known to those skilled in the art; see, for example, Mannervik, 1985, *Meth. Enzymol.* 113, 490–495 and Maiorino et al., 1990, *Meth. Enzymol.* 186, 448–457. Briefly, the conversion of GSH to GSSG can be monitored by coupling that reaction with the oxidation of NADPH to NADP+ and measuring the latter reaction spectrophotometrically. Formation of dityrosine from tyrosine can be measured fluorometrically; see, for example, Anderson, 1964, *Biochim. Biphys. Acta* 93, 213–215 and Fetterer et al., 1990, *J. Parasitol.* 76, 619–624.

The present invention also includes a test kit to identify a compound capable of inhibiting glutathione peroxidase activity of a parasitic helminth. Such a test kit includes an isolated *D. immitis* Gp29 protein having glutathione peroxidase activity and a means for determining the extent of inhibition of glutathione peroxidase activity in the presence of (i.e., effected by) a putative inhibitory compound.

Inhibitors isolated by such a method, and/or test kit, can be used to inhibit any glutathione peroxidase that is susceptible to such an inhibitor. Preferred glutathione peroxidases to inhibit are those produced by parasitic helminths. A particularly preferred glutathione peroxidase inhibitor of the present invention is capable of protecting an animal from heartworm. It is also within the scope of the present invention to use inhibitors of the present invention to target glutathione peroxidase disorders in animals.

Therapeutic compositions comprising glutathione peroxidase-inhibitory compounds of the present invention can be administered to animals in an effective manner to protect animals from disease caused by the targeted glutathione peroxidases. Effective amounts and dosing regimens can be determined using techniques known to those skilled in the art.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Such techniques are known to those skilled in the art.

It is also within the scope of the present invention to use isolated *D. immitis* Gp29 proteins, mimetopes, nucleic acid molecules and antibodies as diagnostic reagents to detect infection by parasitic helminths of the present invention. Such diagnostic reagents can be supplemented with additional compounds that can detect other phases of the helminth's life cycle.

The following examples are provided for the purposes of illustration and are not intended to limit the scope of the present invention.

EXAMPLES

The following examples include a number of recombinant DNA and protein chemistry techniques which are known to those skilled in the art; see, for example, Sambrook et al., ibid.

EXAMPLE 1

This Example demonstrates that a soluble *D. immitis* Gp29 protein is produced in 0-hour L3, 6-day L4 and adult *D. immitis*, as detected by a polyclonal antisera that selectively binds to *B. malayi* Gp29.

The following samples were prepared as described in Grieve et al., PCT International Publication No. WO 92/13560, published Aug. 20, 1992: (a) soluble antigens from 0-hour *D. immitis* L3 (collected directly from the mosquito proboscis); (b) soluble antigens from 6-day L4 cultivated in vitro for 6 days; (c) excretory/secretory antigens from 6-day L4; and (d) soluble antigens from adult female worms. The samples were probed with a rabbit polyclonal antiserum raised to a gel-purified preparation of the major water-soluble surface glycoprotein (Gp29) of adult *B. malayi* (see Selkirk et al., 1990, ibid.) in a Western blot analysis as follows. About 3 μg of each of the samples was subjected to SDS-PAGE through an about 12 percent polyacrylamide gel. Proteins in the gel were transferred onto nitrocellulose following standard procedures. The transferred proteins were probed, using standard immunoblot techniques, with a rabbit anti-*B. malayi* Gp29 antiserum, prepared by immunizing a rabbit with 29-kD *B. malayi* protein recovered from a polyacrylamide gel; see Selkirk et al., 1990, ibid. The anti-*B. malayi* Gp29 antiserum detected a 29-kD band in the 0-hour L3, 6-day L4 and adult soluble antigen preparations as well as in the L4 excretory/secretory antigen preparation. The 29-kD protein was not detected to a significant extent in insoluble pellet fractions of L4. Western blot analysis using normal rabbit sera did not detect a protein of 29 kD. Neither did a rabbit antiserum to the Di22 ladder protein (encoded by the nucleic acid sequence described in Culpepper et al., 1992, *Mol. Biochem. Parasitol.* 54, 51–62) recognize a 29-kD protein, although such an antiserum bound to a different protein of 30 kD, as well as to other ladder proteins. This result indicates that the anti-29-kD *B. malayi* antiserum was sufficiently selective so as not to recognize (i.e., bind to) the immunodominant ladder proteins, one of which migrates at 30 kD.

These results suggest that *D. immitis* begins expressing a significant amount of Gp29 even prior to infection of L3 into a host animal. As such, *D. immitis* Gp29 proteins are good candidates for vaccines against heartworm larvae even during early stages of development after infection into a host animal.

EXAMPLE 2

This Example discloses the isolation and sequencing of *D. immitis* Gp29 nucleic acid molecules of the present invention.

Total RNA was extracted from adult female *D. immitis* worms using an acid-guanidinium-phenol-chloroform method similar to that described by Chomczynski et al., 1987, *Anal. Biochem.* 162, p. 156–159. Approximately 15 worms were used in the RNA preparation. Poly A+ selected RNA was separated from total RNA by oligo-dT cellulose chromatography using Oligo dT cellulose from Collaborative Research Inc., Waltham, Mass., according to the method recommended by the manufacturer.

A *D. immitis* adult female cDNA expression library was constructed in lambda (λ) Uni-ZAP™XR vector (available from Stratagene Cloning Systems, La Jolla, Calif.) using Stratagene's ZAP-cDNA Synthesis Kit® protocol and about 5–6 μg of adult female poly A+ RNA. The resultant library was amplified to a titer of about $1.4 \times 10^9$ pfu/ml with about 97% recombinants.

A *D. immitis* Gp29 nucleic acid molecule of about 660 nucleotides, representing a partial *D. immitis* Gp29 gene and denoted $nGp29_{660}$, was PCR amplified from the *D. immitis* adult female cDNA expression library using two primers designed from the published sequence of the *B. pahangi* Gp29 gene (GenBank data base accession number X63365). That this method worked was surprising since the nucleic acid sequence of *D. immitis* $nGp29_{726}$ (the determination of which is disclosed below) is only about 77 percent homologous to that of (the coding regions of) the genes encoding *B. pahangi* Gp29, *B. pahangi* Gp29 or *W. bancrofti* Gp29.

The two primers designed to obtain *D. immitis* Gp29 nucleic acid molecule $nGp29_{660}$ from the *D. immitis* adult female cDNA library, using standard techniques, include an oligonucleotide having SEQ ID NO:3, namely 5' GGAAT-TCATGTCCGCACAACTTTTGATTTTATCGC 3' (denoted EC4; EcoRI site in bold) and an oligonucleotide having SEQ ID NO:4, namely 5' GGAAT-TCAATTTCACGTTCCAGTTCATCG 3' (denoted EC5; EcoRI site in bold).

Upon amplification, *D. immitis* nucleic acid molecule $nGp29_{660}$ was gel purified, electroeluted and cloned into the cloning vector pCR II (available from Invitrogen, San Diego, Calif.) following manufacturer's instructions, thereby forming recombinant vector $pCRII-nGp29_{660}$. The nucleotide sequence of $nGp29_{660}$ was determined and found to include nucleotides from about 1 to about 660 of SEQ ID NO:1, the production of which is described in more detail below.

A *D. immitis* Gp29 nucleic acid molecule of about 726 nucleotides, denoted $nGp29_{726}$, was obtained by screening the *D. immitis* adult female cDNA expression library with radiolabeled oligonucleotide EC5 as a probe, under stringent (i.e., standard) hybridization conditions as described in Sambrook et al., ibid. Plaques which hybridized with the probe were rescreened and plaque purified. The plaque-purified clone including *D. immitis* nucleic acid sequence $nGp29_{726}$ was converted into a double stranded recombinant molecule, herein denoted as $p\beta gal-nGp 29_{726}$ (capable of encoding the fusion protein $\beta GAL-Pgp29_{726}$), using R408 helper phage and XL1-Blue *E. coli* according to the in vivo excision protocol described in the Stratagene ZAP-cDNA Synthesis Kit. Double stranded plasmid DNA was prepared using an alkaline lysis protocol, such as that described in Sambrook et al., ibid. Recombinant molecule pβgal-$nGp29_{726}$ was digested with EcoRI and XhoI restriction endonucleases to release a *D. immitis* nucleic acid molecule of about 726 nucleotides, denoted $nGp29_{726}$.

*D. immitis* nucleic acid molecule $nGp29_{726}$ was submitted to nucleic acid sequencing using the Sanger dideoxy chain termination method, as described in Sambrook et al., ibid. An about 726-nucleotide consensus sequence of *D. immitis* nucleic acid sequence $nGp29_{726}$ was determined and is presented as SEQ ID NO:1. SEQ ID NO:1 apparently encodes a protein of about 219 amino acids, denoted $PGp29_{219}$, the amino acid sequence of which is presented in SEQ ID NO:2. SEQ ID NO:1 includes a stop codon spanning nucleotides about 659 through about 661. Although SEQ ID NO:1 encodes a protein of about the expected size (i.e., predicted size of about 29 kD), the actual translation initiation site of the protein is not contained within this cDNA clone. The protein comprising SEQ ID NO:2, denoted $PGp29_{219}$, has an estimated pI of about 5.89.

A homology search comparing the amino acid sequence of $PGp29_{219}$ to the non-redundant protein sequence database was performed through the National Center for Biotechnology Information using the BLAST network. This database includes SwissProt+PIR+SPUpdate+GenPept+GpUpdate. The search was performed using SEQ ID NO:2. SEQ ID NO:2 was about 37 percent homologous to the coding region of human plasma glutathione peroxidase (for the sequence of human plasma glutathione peroxidase, see, for example, Takahashi et al., 1987, *Arch. Biochem. Biophys.* 256, 677–687), about 42 percent homologous to the coding region of human liver glutathione peroxidase (GenBank data base accession number P07203, about 73 percent homologous to the coding region of *W. bancrofti* Gp29 (GenBank data base accession number X69126), and about 74 percent homologous both to *B. pahangi* Gp29 (Genbank data base accession number X63365) and to *B. malayi* Gp29 (Genbank accession numbers X69127) coding regions.

EXAMPLE 3

This Example discloses the production of a recombinant cell of the present invention.

Recombinant molecule $pHis-nGp29_{658}$, containing a *D. immitis* Gp29 nucleic acid molecule spanning nucleotides from about 1 through about 658 of SEQ ID NO:1 operatively linked to trc transcription control sequences and to a fusion sequence encoding a poly-histidine segment comprising 6 histidines was produced in the following manner. An about 658-nucleotide DNA fragment containing nucleotides spanning from about 1 through about 658 of SEQ ID NO:1, called $nGp29_{658}$, was PCR amplified from recombinant molecule $p\beta gal-nGp29_{726}$, produced as described in Example 2, using a primer oligonucleotide having SEQ ID NO:5, namely 5' CGGGATCCCATGAGCATACAACTTC 3' (denoted Gp29 SEN; BamHI site in bold) and a primer oligonucleotide having SEQ ID NO:6, namely 5' CGGAAT-TCCTTAAATTTCACGTTCCAATTCATCGATAAA 3' (denoted Gp29 ANT; EcoRI site in bold). The PCR product was digested with BamHI and EcoRI restriction endonucleases, gel purified and subcloned into expression vector pTrcHisB (available from Invitrogen) that had been cleaved with BamHI and EcoRI. The resulting recombinant molecule, denoted $pHis-nGp29_{658}$, was transformed into *E. coli* to form recombinant cell *E. coli*:$pHis-nGp29_{658}$.

EXAMPLE 4

This Example discloses the production of a *D. immitis* Gp29 protein of the present invention by a recombinant cell of the present invention.

Recombinant cell *E. coli*:$pHis-nGp29_{658}$, produced as described in Example 3, was cultured in shake flasks containing an enriched bacterial growth medium containing about 0.1 mg/ml ampicillin at about 37° C. When the cells reached an $OD_{600}$ of about 0.3, expression of *D. immitis* $nGp29_{658}$ was induced by addition of about 1 mM isopropyl-β-D-thiogalactoside (IPTG), and the cells cultured for about 3 hours at about 37° C. Protein production was monitored by SDS PAGE of recombinant cell lysates, followed by Coomassie blue staining, using standard techniques. Recombinant cell *E. coli*:$pHis-nGp29_{658}$ produced a fusion protein, denoted herein as $PHIS-PGp29_{658}$, that migrated with an apparent molecular weight of about 32 kD. Such a protein was not produced by cells transformed with the pTrcHisB plasmid lacking a *D. immitis* nucleic acid molecule insert.

Immunoblot analysis of recombinant cell *E. coli*:pHis-nGp 29$_{658}$ lysates indicated that the 32-kD protein was able to bind to a T7 tag monoclonal antibody (available from Novagen, Inc., Madison, Wis.) directed against the fusion portion of the recombinant PHIS-PGp29$_{658}$ fusion protein.

EXAMPLE 5

This Example describes an expression vector useful in the present invention.

The about 2545-bp (base pair) expression vector TrpT$^2$ori/T7-RSET-B contains the following nucleotide segments. A 1990-bp PvuII to AatII fragment from pUC19 containing the ampicillin resistance gene and *E. coli* of replication; a 130-bp PvuII to BglII synthetic DNA fragment constructed to contain the trp promoter and operator (−35, −10 sequence) and the first 14 amino acids of the trp leader peptide (LE peptide); a BglII to XbaI 55-bp segment from pGEMEX-1 (Promega, Madison Wis.) which contains the T7 promoter; a 170-bp XbaI to EcoRI segment from pRSET-B (Invitrogen, San Diego Calif.) which contains the T7-S10 translational enhancer, the His$_6$ fusion, the 14-amino acid S10 leader fusion, an enterokinase cleavage site and the multiple cloning site; and an about 200-bp fragment containing synthetic translational and transcription termination signals including the T$_1$ translation terminators in all three reading frames, an RNA stabilization sequence from *Bacillus thurengiensis* crystal protein and the T$_2$ rho-independent transcription terminator from the trpA operon.

EXAMPLE 6

This Example describes the production of another *D. immitis* Gp29 protein of the present invention.

Recombinant molecule pTrp-nGp29$_{658}$, containing a *D. immitis* Gp29 nucleic acid molecule spanning nucleotides from about 1 through about 658 of SEQ ID NO:1 operatively linked to trp transcription control sequences and to a fusion sequence encoding a poly-histidine segment comprising 6 histidines was produced in the following manner. The PCR product of nucleic acid molecule nGp29$_{658}$, produced as described in Example 3, was digested with BamHI and EcoRI restriction endonucleases, gel purified and subcloned into expression vector TrpT$^2$ori/T7-RSET-B, produced as described in Example 5, that had been cleaved with BamHI and EcoRI. The resulting recombinant molecule, denoted pTrp-nGp29$_{658}$, was transformed into *E. coli* to form recombinant cell *E. coli*:pTrp-nGp29$_{658}$.

Recombinant cell *E. coli*:pTrp-nGp29$_{658}$ was cultured in shake flasks containing an enriched bacterial growth medium containing about 0.1 mg/ml ampicillin and about 0.2 mg/ml tryptophan at about 37° C. When the cells reached an OD$_{600}$ of about 0.75 to about 1.0, an aliquot of cell suspension equivalent to an OD$_{600}$ of about 0.1 was pelleted by centrifugation and the cells were transferred to about 15 ml of M9 media containing about 0.1 mg/ml ampicillin and about 0.2 mg/ml tryptophan, and grown at about 37° C. When the cells reached an OD$_{600}$ of about 0.75 to about 1.0, expression of *D. immitis* nGp29$_{658}$ was induced by transferring the cells to M9 media containing about 0.1 mg/ml ampicillin, about 0.02 mg/ml tryptophan and about 0.02 mg/ml β-indoleacrylic acid, and the cells cultured for about 3 hours at about 37° C. Protein production was monitored by SDS-PAGE of recombinant cell lysates, followed by Coomassie blue staining, using standard techniques. Recombinant cell *E. coli*:pTrp-nGp29$_{658}$ produced a protein, denoted herein as PTRP-PGp29$_{658}$, that migrated with an apparent molecular weight of about 32 kD.

Immunoblot analysis of recombinant cell *E. coli*:pTrp-nGp 29$_{658}$ lysates indicated that the 32-kD protein was able to bind to a T7 tag monoclonal antibody (available from Novagen, Inc.) directed against the fusion portion of the recombinant PTRP-PGp29$_{658}$ fusion protein.

EXAMPLE 7

This Example describes an expression vector useful in the present invention.

The about 4200-bp expression vector λP$_R$/T$^2$ori/S10HIS-RSET-A 9 contains the following nucleotide segments. A 1990-bp PvuII to AatII fragment from pUC19 containing the ampicillin resistance gene and *E. coli* origin of replication; an 1100-bp PvuII to BglII DNA fragment from vector pRK248cI$^{ts}$ (ATCC#33766) containing the λP$_R$ promoter, the cl$^{857}$λ repressor gene and 22 amino acids of the cro gene regulating lytic growth; a 55-bp BglII to XbaI segment from pGEMEX-1 (available from Promega) which contains the T7 promoter; a 75-bp XbaI to NheI segment from pRSET-B (available from Invitrogen) which contains the T7-S10 translational enhancer and the His$_6$ fusion; an about 825-bp NheI to SstI fragment from pGEMEX-1 containing the 275-amino acid S10 peptide; a multiple cloning site from portions of the pRSET and pUC9 vectors; and an about 140-bp fragment containing synthetic translational and transcription termination signals including the T$_1$ translation terminators in all three reading frames, RNA stabilization sequence from *Bacillus thurengiensis* crystal protein the T$_2$ rho-independent transcription terminator from the trpA operon.

EXAMPLE 8

This Example describes the production of a recombinant cell of the present invention.

Recombinant molecule pλP$_R$-nGp29$_{658}$, containing a *D. immitis* Gp29 nucleic acid molecule spanning nucleotides from about 1 through about 658 of SEQ ID NO:1 operatively linked to λP$_R$ transcription control sequences and to a fusion sequence encoding a poly-histidine segment comprising 6 histidines was produced in the following manner. The PCR product of nucleic acid molecule nGp29$_{658}$, produced as described in Example 3, was digested with BamHI and EcoRI restriction endonucleases, gel purified and subcloned into expression vector λP$_R$/T$^2$ori/S10HIS-RSET-A9, produced as described in Example 7, that had been cleaved with BamHI and EcoRI. The resulting recombinant molecule, denoted pλP$_R$-nGp29$_{658}$, was transformed into *E. coli* to form recombinant cell *E. coli*:pλP$_R$-nGp29$_{658}$. Such a recombinant cell encodes the fusion protein PHIS-PGp29$_{658}$.

EXAMPLE 9

This Example describes the production of a *D. immitis* Gp29 protein of the present invention in a eukaryotic cell.

Recombinant molecule pBBIII-nGp29$_{658}$, containing a *D. immitis* Gp29 nucleic acid molecule spanning nucleotides from about 1 through about 658 of SEQ ID NO:1 operatively linked to baculovirus polyhedron transcription control sequences was produced in the following manner. In order to subclone a Gp29 nucleic acid molecule into baculovirus expression vectors, Gp29 nucleic acid molecule-containing fragments were PCR amplified from pβgal-nGp29$_{726}$ DNA

27

(produced as in Example 2), using a sense primer BvGp29SEN (5' CGCGGATCCTATAATATGAGCATA-CAACTTCTTATTTTATC 3' (SEQ ID NO:7)) and an antisense primer BvGp29 ANT (5' TGCATATAAGGATCCG-TATTAAATTTCACG 3' (SEQ ID NO:8)), which have BamHI sites (indicated in bold) incorporated into the primers. The N-terminal primer was designed from nGp29$_{726}$ sequence with modifications to enhance expression in the baculovirus system.

In order to produce a baculovirus recombinant molecule capable of directing the production of PGp29$_{219}$, the about 690-bp PCR product (referred to as BvGp29) was digested with BamHI and subcloned into the unique BglII site of BlueBacIII (available from Invitrogen) baculovirus shuttle plasmid. The resultant recombinant molecule, denoted pBBIII-nGp29$_{658}$ was verified for proper insert orientation by restriction mapping. Such a recombinant molecule can be co-transfected with a linear Baculogold baculovirus DNA (available from Pharmingen, San Diego, Calif.) into *S. frugiperda* Sf9 cells (donated by the Colorado Bioprocessing Center, Fort Collins, Colo.) to form a recombinant cell denoted *S. frugiperda*:pBBIII-nGP29$_{658}$. Such a recombinant cell can be cultured in order to produce a *D. immitis* Gp29 protein of the present invention, namely PGp29$_{219}$.

EXAMPLE 10

This Example describes the production of a *D. immitis* Gp29 protein of the present invention in a eukaryotic cell as well as the production of a recombinant virus vaccine.

Recombinant molecule pToto2J1-nGP29$_{658}$ comprises a *D. immitis* Gp29 nucleic acid molecule spanning nucleotides from about 1 through about 658 of SEQ ID NO:1 operatively

28 linked to the Sindbis virus subgenomic promoter in Sindbis virus vector Toto2J1 from which the chloramphenicol acetyltransferse (CAT) gene has been removed by restricting the vector with XbaI and XhoI. Toto2J1 is a Sindbis virus expression vector that contains the SP6 RNA polymerase promoter and the entire Sindbis virus genome through to the NsiI restriction site at nucleotide 11452 (i.e., each of the nonstructural polypeptide genes, the subgenomic promoter, and each of the structural polypeptide genes) ligated to an SspI (nucleotide position 7499)/SstI restriction fragment from TRCAT62 which contains the subgenomic promoter, 14 nucleotides of the 5' untranslated sequence of the subgenomic mRNA, the CAT gene, 62 nucleotides of Sindbis virus 3' untranslated sequence, and the Sindbis virus poly-A sequence (see Xiong et al., 1989, *Science* 243, 1188–1191).

Infectious recombinant transcripts are generated from an MluI-linearized form of recombinant molecule pToto2J1-nGp 29$_{658}$ using SP6 RNA Polymerase. The resulting transcripts are transfected into BHK (baby hamster kidney) host cells using techniques as described in Xiong et al., ibid, thereby forming BHK:pToto2J1-nGp29$_{658}$. The resulting recombinant virus can be used as a live vaccine or in an expression system to produce PGp29$_{219}$.

SEQUENCE LISTING

The following Sequence Listing is submitted pursuant to 37 CFR §1.821. A copy in computer readable form is also submitted herewith. The paper and computer readable forms of this Sequence Listing are the same.

---

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 726 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Dirofilaria immitis ( v i i ) IMMEDIATE SOURCE:
        ( A ) LIBRARY: Adult female D. immitis cDNA expression
            library
        ( B ) CLONE: nGp29

( i x ) FEATURE:
        ( A ) NAME/KEY: CDS
        ( B ) LOCATION: 2..659

( x i ) SEQUENCE DESCRIPTION: SEQ ID NO:1:

```
C ATA CAA CTT CTT ATT TTA TCA TAT GCG ATA CTA TTA CAA CTT ATT         4 6
  Ile Gln Leu Leu Ile Leu Ser Tyr Ala Ile Leu Leu Gln Leu Ile
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     | 1   |     |     |     | 5   |     |     |     |     | 10  |     |     |     |     | 15  |     |
| GCA | ACA | CAA | GTG | GCT | GAT | AAG | CAA | CTC | CCA | AAT | CTA | ACA | AAA | CAG | TGT | 94  |
| Ala | Thr | Gln | Val | Ala | Asp | Lys | Gln | Leu | Pro | Asn | Leu | Thr | Lys | Gln | Cys |     |
|     |     |     |     | 20  |     |     |     |     | 25  |     |     |     |     | 30  |     |     |
| GAA | CCA | ACA | AGT | CAG | ACA | ATA | TAT | GAT | TTT | CAT | GTT | CCA | ACA | CTA | GAT | 142 |
| Glu | Pro | Thr | Ser | Gln | Thr | Ile | Tyr | Asp | Phe | His | Val | Pro | Thr | Leu | Asp |     |
|     |     |     | 35  |     |     |     |     | 40  |     |     |     |     | 45  |     |     |     |
| GGT | TCA | GAA | AAA | AGT | TTG | GCA | GAA | TAC | CGC | GGC | AAA | GTT | CTC | TTA | CTC | 190 |
| Gly | Ser | Glu | Lys | Ser | Leu | Ala | Glu | Tyr | Arg | Gly | Lys | Val | Leu | Leu | Leu |     |
|     |     | 50  |     |     |     |     | 55  |     |     |     |     | 60  |     |     |     |     |
| GTC | AAT | GTT | GCC | ACT | TAT | TGT | GCA | TAC | ACC | TTT | CAA | TAC | AAT | GAT | TTC | 238 |
| Val | Asn | Val | Ala | Thr | Tyr | Cys | Ala | Tyr | Thr | Phe | Gln | Tyr | Asn | Asp | Phe |     |
|     | 65  |     |     |     |     | 70  |     |     |     |     | 75  |     |     |     |     |     |
| AAT | CCA | ATG | CTT | GAA | AAT | AAT | TCC | AAT | GGG | ACA | CTA | AAA | ATC | CTG | GCA | 286 |
| Asn | Pro | Met | Leu | Glu | Asn | Asn | Ser | Asn | Gly | Thr | Leu | Lys | Ile | Leu | Ala |     |
| 80  |     |     |     |     | 85  |     |     |     |     | 90  |     |     |     |     | 95  |     |
| TTT | CCA | TGT | AAT | CAA | TTC | CTC | TTG | CAA | GAA | CCG | GCA | GAA | AAT | CAT | GAA | 334 |
| Phe | Pro | Cys | Asn | Gln | Phe | Leu | Leu | Gln | Glu | Pro | Ala | Glu | Asn | His | Glu |     |
|     |     |     |     | 100 |     |     |     |     | 105 |     |     |     |     | 110 |     |     |
| TTA | TTG | AAT | GGA | TTG | AAA | TAT | GTA | AGA | CCT | GGA | AAT | GGT | TGG | GAA | CCG | 382 |
| Leu | Leu | Asn | Gly | Leu | Lys | Tyr | Val | Arg | Pro | Gly | Asn | Gly | Trp | Glu | Pro |     |
|     |     |     | 115 |     |     |     |     | 120 |     |     |     |     | 125 |     |     |     |
| CAC | GGA | AAT | ATG | CAT | ATT | TTC | GGA | AAA | GTT | GAA | GTT | AAT | GGT | GAC | GAT | 430 |
| His | Gly | Asn | Met | His | Ile | Phe | Gly | Lys | Val | Glu | Val | Asn | Gly | Asp | Asp |     |
|     |     | 130 |     |     |     |     | 135 |     |     |     |     | 140 |     |     |     |     |
| CAT | CAT | CCA | CTT | TAT | AAA | TTT | TTG | AAG | GAA | CAT | TGC | CCT | CAA | ACA | GTG | 478 |
| His | His | Pro | Leu | Tyr | Lys | Phe | Leu | Lys | Glu | His | Cys | Pro | Gln | Thr | Val |     |
|     | 145 |     |     |     |     | 150 |     |     |     |     | 155 |     |     |     |     |     |
| CCA | ATA | ATT | GGA | GAC | CGT | CAC | CAA | CTG | ATG | TAC | AAT | CCA | ATC | GGT | ACA | 526 |
| Pro | Ile | Ile | Gly | Asp | Arg | His | Gln | Leu | Met | Tyr | Asn | Pro | Ile | Gly | Thr |     |
| 160 |     |     |     |     | 165 |     |     |     |     | 170 |     |     |     |     | 175 |     |
| AAT | GAT | ATC | ATT | TGG | AAC | TTT | GAA | AAA | TTC | TTA | ATC | GAT | AAA | AAA | GGT | 574 |
| Asn | Asp | Ile | Ile | Trp | Asn | Phe | Glu | Lys | Phe | Leu | Ile | Asp | Lys | Lys | Gly |     |
|     |     |     |     | 180 |     |     |     |     | 185 |     |     |     |     | 190 |     |     |
| CAT | CCA | CGT | TAT | CGT | TTT | CAT | CCT | AGC | GCA | TGG | GTT | CAG | GGA | AGT | GTT | 622 |
| His | Pro | Arg | Tyr | Arg | Phe | His | Pro | Ser | Ala | Trp | Val | Gln | Gly | Ser | Val |     |
|     |     |     | 195 |     |     |     |     | 200 |     |     |     |     | 205 |     |     |     |
| ATA | GCA | CCG | TTT | ATC | GAT | GAA | TTG | GAA | CGT | GAA | ATT | T AATACCGTTA |     |     |     | 669 |
| Ile | Ala | Pro | Phe | Ile | Asp | Glu | Leu | Glu | Arg | Glu | Ile |     |     |     |     |     |
|     |     | 210 |     |     |     |     | 215 |     |     |     |     |     |     |     |     |     |

CTTATATGCA TGATAAATTT CTCACTTTGC GAAATTTTCA CTATATTTTT ATTACCG       726

( 2 ) INFORMATION FOR SEQ ID NO:2:

( i ) SEQUENCE CHARACTERISTICS:
        ( A ) LENGTH: 219 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ile | Gln | Leu | Leu | Ile | Leu | Ser | Tyr | Ala | Ile | Leu | Leu | Gln | Leu | Ile | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Thr | Gln | Val | Ala | Asp | Lys | Gln | Leu | Pro | Asn | Leu | Thr | Lys | Gln | Cys | Glu |
|     |     |     | 20  |     |     |     |     | 25  |     |     |     |     | 30  |     |     |
| Pro | Thr | Ser | Gln | Thr | Ile | Tyr | Asp | Phe | His | Val | Pro | Thr | Leu | Asp | Gly |
|     |     | 35  |     |     |     |     | 40  |     |     |     |     | 45  |     |     |     |
| Ser | Glu | Lys | Ser | Leu | Ala | Glu | Tyr | Arg | Gly | Lys | Val | Leu | Leu | Leu | Val |
|     | 50  |     |     |     |     | 55  |     |     |     |     | 60  |     |     |     |     |

| Asn<br>65 | Val | Ala | Thr | Tyr | Cys<br>70 | Ala | Tyr | Thr | Phe | Gln<br>75 | Tyr | Asn | Asp | Phe | Asn<br>80 |
|---|---|---|---|---|---|---|---|---|---|---|---|---|---|---|---|
| Pro | Met | Leu | Glu | Asn<br>85 | Asn | Ser | Asn | Gly | Thr<br>90 | Leu | Lys | Ile | Leu | Ala<br>95 | Phe |
| Pro | Cys | Asn | Gln<br>100 | Phe | Leu | Leu | Gln | Glu<br>105 | Pro | Ala | Glu | Asn | His<br>110 | Glu | Leu |
| Leu | Asn | Gly<br>115 | Leu | Lys | Tyr | Val | Arg<br>120 | Pro | Gly | Asn | Gly | Trp<br>125 | Glu | Pro | His |
| Gly | Asn<br>130 | Met | His | Ile | Phe | Gly<br>135 | Lys | Val | Glu | Val | Asn<br>140 | Gly | Asp | Asp | His |
| His<br>145 | Pro | Leu | Tyr | Lys | Phe<br>150 | Leu | Lys | Glu | His | Cys<br>155 | Pro | Gln | Thr | Val | Pro<br>160 |
| Ile | Ile | Gly | Asp | Arg<br>165 | His | Gln | Leu | Met | Tyr<br>170 | Asn | Pro | Ile | Gly | Thr<br>175 | Asn |
| Asp | Ile | Ile | Trp<br>180 | Asn | Phe | Glu | Lys | Phe<br>185 | Leu | Ile | Asp | Lys | Lys<br>190 | Gly | His |
| Pro | Arg | Tyr<br>195 | Arg | Phe | His | Pro | Ser<br>200 | Ala | Trp | Val | Gln | Gly<br>205 | Ser | Val | Ile |
| Ala | Pro<br>210 | Phe | Ile | Asp | Glu | Leu<br>215 | Glu | Arg | Glu | Ile | | | | | |

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GGAATTCATG TCCGCACAAC TTTTGATTTT ATCGC     35

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GGAATTCAAT TTCACGTTCC AGTTCATCG     29

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CGGGATCCCA TGAGCATACA ACTTC     25

( 2 ) INFORMATION FOR SEQ ID NO:6:

( i ) SEQUENCE CHARACTERISTICS:
        ( A ) LENGTH: 39 base pairs

-continued ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

CGGAATTCCT TAAATTTCAC GTTCCAATTC ATCGATAAA 39

( 2 ) INFORMATION FOR SEQ ID NO:7:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

CGCGGATCCT ATAATATGAG CATACAACTT CTTATTTTAT C 41

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:8:

TGCATATAAG GATCCGTATT AAATTTCACG 30

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule having a nucleic acid sequence encoding a *Dirofilaria immitis* Gp29 protein.

2. The nucleic acid molecule of claim 1, wherein said nucleic acid molecule comprises a nucleic acid sequence having SEQ ID NO:1.

3. The nucleic acid molecule of claim 1, wherein said nucleic acid sequence encodes an enzyme having glutathione peroxidase activity.

4. The nucleic acid molecule of claim 1, wherein said nucleic acid molecule comprises a nucleic acid molecule selected from the group consisting of $nGp29_{726}$, $nGp29_{658}$ and $nGp29_{660}$.

5. A recombinant molecule comprising an isolated nucleic acid molecule set forth in claim 1 operatively linked to a transcription control sequence.

6. A recombinant cell line comprising a recombinant molecule as set forth in claim 5.

7. A recombinant cell line comprising a nucleic acid molecule as set forth in claim 1, wherein said cell line produces said protein.

8. The recombinant cell of claim 7, wherein said recombinant cell is of the genus Salmonella.

9. A method to produce an isolated *D. immitis* Gp29 protein comprising culturing in an effective medium a recombinant cell line comprising a nucleic acid molecule as set forth in claim 1 to produce said protein.

* * * * *